United States Patent
Saito et al.

(10) Patent No.: US 6,325,993 B1
(45) Date of Patent: Dec. 4, 2001

(54) ORAL ADHESIVE SHEET AND ORAL ADHESIVE PREPARATION

(75) Inventors: Junichi Saito; Yuichi Inoue, both of Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/515,011

(22) Filed: Feb. 29, 2000

(30) Foreign Application Priority Data

Mar. 3, 1999 (JP) .................................................. 11-056249
May 12, 1999 (JP) .................................................. 11-130768

(51) Int. Cl.$^7$ .............................. A61K 7/16; A61F 13/00
(52) U.S. Cl. ........................... 424/49; 424/434; 424/435; 442/19; 602/52; 602/76
(58) Field of Search .................................. 424/434, 435; 442/19; 602/52, 76

(56) References Cited

U.S. PATENT DOCUMENTS

| 3,972,995 | 8/1976 | Tsuk et al. . | |
|---|---|---|---|
| 5,750,134 | * 5/1998 | Scholz et al. | ........................ 424/434 |
| 5,827,525 | 10/1998 | Liao et al. . | |

FOREIGN PATENT DOCUMENTS 0156080    10/1985  (EP) .
91/06290   5/1991   (WO) .

OTHER PUBLICATIONS

Japanese Abstract; JP63309572 dated Dec. 1988 (Sekisui Chem Ind Co Ltd); Database WPI, Week 198905, Derwent Publications Ltd., London, GB.

* cited by examiner

*Primary Examiner*—Frederick Krass
*Assistant Examiner*—Donna Jagoe
(74) *Attorney, Agent, or Firm*—Kilyk&Bowersox, PLLC

(57) ABSTRACT

An oral adhesive preparation has a substrate and a pressure-sensitive adhesive layer provided on at least one surface of the substrate, in which the pressure-sensitive adhesive layer contains a medicine, and is substantially insoluble in water or absorbs substantially no water. Further, an oral adhesive sheet comprising a separator release-treated on one or both surfaces thereof and a plurality of sections for application to oral mucous membrane mounted on at least one surface of the separator in a specified 2 to 5 by 2 to 5 arrangement with a specified proportion of a minimum inner diameter, Dp, of an incircle passing a center of gravity, W, of a section to a shortest distance, Di, of an adjacent section is 1.5 to 6. The substrate is preferably cloth such as non-woven fabric. Sections containing a local anesthetic can be used in surface anesthesia in dentistry.

17 Claims, 1 Drawing Sheet

ORAL ADHESIVE SHEET AND ORAL ADHESIVE PREPARATION

BACKGROUND OF THE INVENTION

1. Field of the Invention

The present invention relates to an adhesive preparation that is applied in the mouth and used upon administration of a medicine in the mouth. Further, the present invention relates to an oral adhesive sheet and more particularly to an oral adhesive sheet including a separator and a plurality of sections mounted on the separator, having a pressure-sensitive adhesive layer containing a medicine for adhering to the oral mucous membrane such as gingival mucous membrane so as to apply the medicine through the mucous membrane to improve handling property of the adhesive sheet.

2. Description of the Related Art

Heretofore, various methods have been known for the administration of medicines in the mouth. For example, there have been known methods using solution, ointment, jelly, spray, troche, buccal tablet, sublingual tablet, etc., respectively.

Recently, as a preparation that has good adhesiveness even in an oral cavity mucous membrane wetted with moisture such as saliva, there has been proposed an oral adhesive preparation having a pressure-sensitive adhesive layer containing a medicine, a base (major component) of the pressure-sensitive adhesive layer comprising a water soluble or water swellable polymer. For example, a mucous membrane-adhering preparation having a substrate and a mucous membrane adhering pressure-sensitive adhesive layer on the substrate, containing an alginic acid ester and a medicine (JP-A-61-30516), an external film preparation containing hydroxypropyl cellulose as a major component and a pharmaceutical preparation (JP-A-62-63513), local anesthetic adhesive preparation for application to gingiva, having a pressure-sensitive adhesive layer comprising a water-soluble polymer such as polyvinylpyrrolidone and a water-insoluble or water-swellable polymeric substance such as polyvinyl acetate and a physiologically active component (JP-A-1-272521), an oral application substrate of a two-layer structure produced by casting and drying a liquid containing a polyacrylic acid salt, a carboxyvinyl polymer and polyvinyl alcohol (JP-A-5-310561), etc.

In the case of the conventional oral adhesive preparations containing water-soluble or water-swellable polymer as a basis (major component) of the adhesive layer, the water-soluble or water-swellable polymer absorbs the moisture present on the surface of adherend (surface of the mucous membrane in the oral cavity). This causes the surface of the adhesive layer to contact the surface of the adherend to effect adhesion.

As means for administering a medicine through the mucous membrane, there have been developed sheet-form adhesive preparation having good adhesion (pressure-sensitive adhesion) even at wetted site. Many attempts from the viewpoint of composition have been made on such a sheet-form adhesive preparation. For example, adhesive preparations are designed to use a water-soluble or water-swellable polymer as a basis for adhesive in order to impart adhesiveness to the wetted site.

On the other hand, as means for administering a medicine through skin, there have been developed and widely used various endermic pharmaceutical preparations using pressure-sensitive adhesives. Such endermic pharmaceutical preparations include various forms. As typical examples, mention is made of adhesive sheet-type adhesive preparations having a non-water-soluble pressure-sensitive adhesive layer containing a medicine and a support layer. These types of adhesive preparations have not been used as an oral adhesive preparation. This is because it has been recognized that the non-water-soluble pressure-sensitive adhesive layer generally shows no sufficient adhesion to an adherend that is wetted with moisture.

SUMMARY OF THE INVENTION

However, it sometimes occurs that such an oral adhesive preparation is detached and removed due to the swelling or dissolution of the water-soluble or water-swelling polymer in the adhesive layer with water or that the medicine seeps and flows away from the adhesive layer. When the adhesive layer deforms to a large extent as a result of the swelling of a water-swellable polymer, the user will feel the existence of foreign body in the mouth. In case where no such problem as detachment or falling off does occur, generally adhesion with a strong adhesive strength occurs so that when it is attempted to detach the dressing preparation in a short time (that is, it is attempted to detach it quickly), pain is accompanied or there is the danger that the mucous membrane in the mouth is damaged.

Further, when a sheet-form adhesive preparation is applied into the mouth, adhesive preparation for oral application, in particular one for application to gingival mucous membrane are used in the form of small sections (application sections) of 1 cm×1 cm since the area at the site of application is small as compared with the area of external skin surface. Generally, the adhesive preparation for oral application must have pharmacological effects, acceptable application feeling, adhesion, etc. In addition, in the field of medical treatment, for example, when surface anesthesia is performed in the region of dentistry, the property of easy handling upon its application is also important so that the form of product is also one of the important elements. For this reason, a product having a product form that is easy to handle in the field of therapy is desired.

Under the circumstances, an object of the present invention is to provide an oral adhesive preparation that adheres to the oral mucous membrane with an adhesive strength agreeable to adhesion in the oral cavity, that causes no detachment or falling off or seeping or flowing away of the medicine, that gives substantially no foreign feeling upon application and that can be readily detached in a short time.

Another object of the present invention is to provide an adhesive preparation used by applying in oral cavity that is of a form such that it can be used effectively in view of easy handling in the field of therapy.

As a result of intensive research, the present inventors have found that a hydrophobic pressure-sensitive adhesive layer, that is, a pressure-sensitive adhesive layer that is substantially insoluble in water (non-water-soluble pressure-sensitive adhesive) or a pressure-sensitive adhesive layer that absorbs substantially no water is difficult to adhere to an adherend when water is present on the surface of the adherend in such a large amount that the water behaves as a fluid but it can adhere to the surface of the adherend by removing the fluid water that is present on the surface of the adherend in a large amount to such an extent that the surface of the adherend is wetted with moisture more or less.

Furthermore, the present inventors have found that mounting a plurality of sections each comprising a pressure-sensitive adhesive layer containing a medicine and a substrate on a separator generally square in shape in a specified arrangement or pattern gives rise to an adhesive sheet having an excellent handling property. The present invention has been accomplished based on the above discoveries.

Therefore, the present invention provide the followings:
1) An oral adhesive preparation comprising a substrate and a pressure-sensitive adhesive layer provided on at least one surface of the substrate, wherein the pressure-sensitive adhesive layer contains a medicine, and is substantially insoluble in water or absorbs substantially no water.
2) The oral adhesive preparation as described in 1 above, wherein the substrate comprises a non-woven fabric that has a basis weight of 20 to 150 g/m$^2$ as prescribed in JIS-L1085 and a thickness of 0.1 to 1.0 mm as prescribed in JIS-L1085.
3) The oral adhesive preparation as described in 2 above, wherein the non-woven fabric has a bending resistance (45° cantilever method) of 10 to 80 mm as prescribed in JIS-L1085.
4) The oral adhesive preparation as described in 2 above, wherein the non-woven fabric comprises as a major component at least one of polyolefin fiber and polyester fiber.
5) The oral adhesive preparation as described in 2 above, wherein the non-woven fabric is spun lace non-woven fabric.
6) The oral adhesive preparation as described in 1 above, wherein a combination of the pressure-sensitive adhesive layer that contains a medicine and the substrate has a bending resistance (45° cantilever method) of 15 to 60 mm as prescribed in JIS-L1085.
7) The oral adhesive preparation as described in 1 above, wherein the pressure-sensitive adhesive layer that is substantially insoluble in water or absorbs substantially no water comprises at least one member selected from the group consisting of acrylic-based polymers, rubber-based adhesives, silicone-based adhesives, vinyl ether-based adhesives, and vinyl ester-based adhesives.
8) The oral adhesive preparation as described in 7 above, wherein the adhesive comprising an acrylic-based polymer is a copolymer of (meth)acrylic acid alkyl ester and (meth)acrylic acid.
9) The oral adhesive preparation as described in 1 above, wherein the copolymer of (meth)acrylic acid alkyl ester and (meth)acrylic acid comprises a copolymer of 65 to 99% by weight of (meth)acrylic alkyl ester and 1 to 35% by weight of (meth)acrylic acid.
10) The oral adhesive preparation as described in 1 above, wherein the medicine is a local anesthesia.
11) The oral adhesive preparation as described in 10 above, wherein the local anesthesia is at least one member selected from the group consisting of lidocaine, cocaine, procaine, chloroprocaine, tetracaine, benzocaine, mepivacaine, prilocaine, bupivacaine, dibucaine, propoxycaine, etidocaine, dichlonine, and pharmacologically acceptable salts thereof.
12) The oral adhesive preparation as described in 1 above, wherein the medicine is a systemic medicine.
13) The oral adhesive preparation as described in 12 above, wherein the systemic medicine is at least one member selected from the group consisting of corticosteroids, analgesic antiphlogistics, narcotic sedatives, tranquilizers, antihypertensives, hypotensive diuretics, antibiotics, systemic anesthesia, antibacterial agents, antifungal agents, vitamins, coronary vessel dilators, antihistamines, expectorants, sex hormones, antidepressants, brain circulation improvers, antiemetics, antineoplastics, antiulcers, and biomedicines.
14) An oral adhesive sheet comprising a separator release-treated on one or both surfaces thereof and a plurality of sections for application to oral mucous membrane mounted on at least one surface of the separator, wherein the sections comprise each a flexible support and a pressure-sensitive adhesive layer on one surface of the substrate, wherein the sections are adhered and arranged on the separator in 2 to 5 columns by 2 to 5 arrows, each section being in a substantially equivalent distance from adjacent section, and wherein inter-section distance between any adjacent two sections is set such that a proportion of a minimum inner diameter, Dp, of an incircle passing a center of gravity, W, of a section to a shortest distance, Di, of an adjacent section is 1.5 to 6.
15) The oral adhesive sheet as described in 14 above, wherein the substrate is cloth.
16) The oral adhesive sheet as described in 14 above, wherein the medicine is a local anesthetic.
17) The oral adhesive sheet as described in 14 above, wherein the sheet shows an angle of deflection of 10 degrees or less when held horizontally at a prehension width of 5 mm at one of two points on a peripheral portion of the separator defining a largest linear length.
18) The oral adhesive sheet as described in 14 above, wherein the section is a section for application to gingival mucous membrane.
19) The oral adhesive sheet as described in 14 above, wherein the section is a section as described in 1 above.

The oral adhesive preparation of the present invention can adhere to the mucous membrane in the oral cavity with moderate adhesive force and can be readily detached in a short time. In particular, it can administer a drug efficiently without causing falling-off of the adhesive layer or seeping or flowing away of the drug, and gives no feeling of non-self or foreign feeling so that it is practically very useful.

Since the oral adhesive sheet has the above-described construction, it is excellent in handling property upon detaching the sections from the separator. At t the same time, because of the arrangement of sections having each a suitable size mounted in a number required for in the field of actual therapy, a reduction in operation time for the therapy can be expected. Further, the proportion of the size of each section to the inter-section distance set to specific values increases processability upon production to thereby increase productivity.

The above and other objects, effects, features and advantages of the present invention will become more apparent from the following description of preferred embodiments.

DETAILED DESCRIPTION OF THE INVENTION

Figure 1:
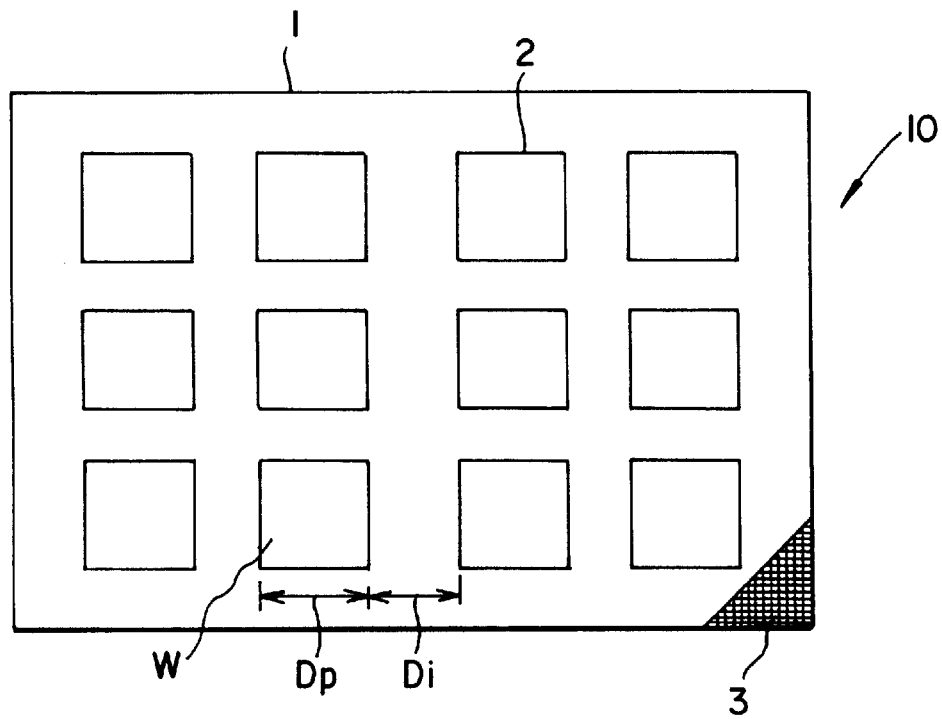
FIG. 1 is a plan view showing an example of an oral adhesive sheet of the present invention.
Figure 2:
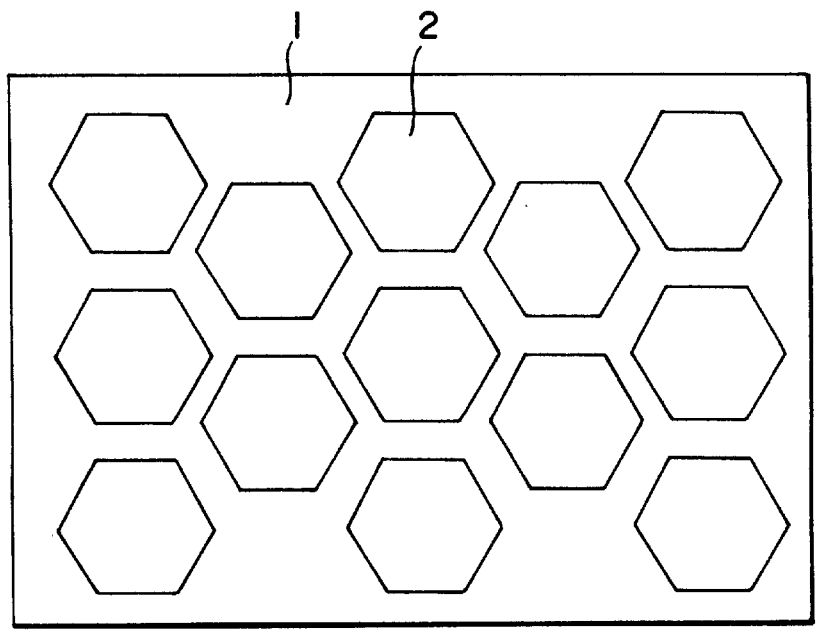
FIG. 2 is a plan view showing another example of an oral adhesive sheet of the present invention.

In the present invention, the term "pressure-sensitive adhesive layer that is substantially insoluble in water or that absorbs substantially no water" means an "adhesive layer formed from as a major component an adhesive polymer that dissolves in an amount of 5% by weight or less in a sufficient amount of water at 20° C. and shows pressure-sensitive adhesiveness at normal temperature (room temperature, e.g., 20° C.) and/or an adhesive polymer that absorbs water in an amount of 5% by weight or less when a sufficient amount of water is present and shows pressure-sensitive adhesiveness at normal temperature (room temperature, e.g., 20° C.), the basis of % by weight being total weight of the polymer."

In applying the oral adhesive preparation of the present invention, if a large amount of water is present at a site in the oral cavity where the adhesive preparation is to be applied, the water is wiped off or otherwise removed before application. Of course, if the water at the application site is in a small amount and no trouble is caused thereby, the adhesive preparation may be applied without performing water removal operation. Further, it has been confirmed that if moisture is present in a relatively large amount on the surface of oral cavity, the adhesive preparation of the invention is kept attached to the surface of oral cavity for a time sufficient for the medicine contained to be administered depending on the kind of medicine.

For example, in actual treatment dentists dries the oral mucous membrane such as gingiva by air drying in most cases by use of an air syringe. The drying with an air syringe is performed by blowing for only several seconds because cooling due to evaporation of water often causes pain. Therefore, in many cases, water is removed only insufficiently and more or less water remains. In such a case, the oral adhesive preparation of the present invention adheres to the oral mucous membrane moderately weakly and is detached readily.

In actual administration of medicines in the oral cavity, the pressure-sensitive adhesive layer of the adhesive preparation is not required to have such a strong adhesiveness as is required for industrial application. Instead, weak adhesiveness and short adhesion time are sufficient for practical use. Also, as will be described later on, it is sometimes the case that rather weak adhesiveness and short adhesion time are desirable.

The oral adhesive preparation of the present invention will lose its adhesiveness in a relatively short time when a relatively large amount of moisture is present on the surface or when the surface of the adherend is relatively soft and it will maintain its adhesiveness for a relatively long time when a relatively small amount of moisture is present on the surface of the adherend or when the surface of the adherend is relatively hard. Therefore, generally, there is the tendency that on the surface of mucous membrane on the inner surface of bucca, the adhesive force is weak and adhesion time is short, and on the other hand, on the surface of gingiva, the adhesive force is relatively strong and the adhesion time is relatively long.

In therapeutic activity in the region of dentistry, it is desirable that the administration of local anesthesia be performed in a time as short as possible. Accordingly, oral adhesive preparations are required to exhibit their effect in a short time and exhibit weak adhesiveness such that they are detached readily in a short time. The above-mentioned conventional oral adhesive preparation containing a conventional water-soluble or water-swellable polymer as a basis has high adhesive strength to the oral mucous membrane as described above so that when it is detached in a short time after the application, there is the fear that pain is accompanied or the mucous membrane is damaged. Many of them are designed to slowly release the medicine and no sufficient pharmacological effect can be obtained in a short time.

In contrast, the oral adhesive preparation of the present invention having a medicine-containing, pressure-sensitive adhesive layer that is substantially insoluble in water or that absorbs substantially no water exhibits its pharmacological effect in a short time after the application when it is applied in the oral cavity since the medicine has relatively low affinity for the adhesive so that the medicine is released burstingly.

Therefore, the oral adhesive preparation of the present invention in particular carries local anesthesia as the medicine and is suitable for use in surface anesthesia in the region of dentistry.

Further, the pressure-sensitive adhesive layer that is substantially insoluble in water or that absorbs substantially no water causes no detachment nor falling off due to swelling, causes no seeping nor flowing away of the medicine, gives no bitter taste of the medicine, causes no pharmacological effect to be exhibited at undesirable site, or allows high availability of the medicine. Further, it undergoes substantially no deformation due to swelling so that it tends to give no feeling of the existence of foreign matter.

The oral cavity is a site that has a very sharp sensibility and constitutes a complicated and narrow space as surrounded by the teeth, tongue, etc. so that the orally applied adhesive preparation is required to have good handling property and give less feeling of such as the feeling of the existence of foreign matter or the feeling of propping up when it is applied. Generally, the pressure-sensitive adhesive layer is flexible and has sufficient follow-up properties within a practical thickness range. Therefore, the handling property in the oral cavity and the feeling of the existence of foreign matter of the adhesive preparation largely depends on the physical properties of the substrate supporting the pressure-sensitive adhesive layer. That is, if the substrate is flexible, the adhesive preparation can be applied to an uneven surface in the oral cavity beneficially and in addition the feeling of non-self is relieved.

Therefore, in the oral adhesive preparation, it is important that the medicine-containing, pressure-sensitive adhesive layer that is substantially insoluble in water or that absorbs substantially no water is supported by a flexible substrate.

The substrate used in the oral adhesive preparation of the present invention is not particularly limited in its material so far as it improves the handling property of the oral adhesive preparation in the oral cavity upon actual use and has moderate flexibility so as to relieve the feeling of non-self upon application. More particularly, mention may be made of cloths, examples of which include simple films or laminate films composed of one of synthetic resins, for example, polyolefins such as polyethylene and polypropylene, polyesters such as polyethylene terephthalate, polyamides such as nylon, polyvinyl chloride, plasticized polyvinyl chloride, plasticized vinyl acetate-vinyl chloride copolymers, polyvinylidene chloride, ethylene-vinyl acetate copolymers, cellulose acetate, ethylcellulose, ethylene-ethyl acrylate copolymers, polytetrafluoroethylene, polyurethane, ionomer resins; porous films or sheets fabricated using at least one selected from rubbers, the above synthetic resins, polyesters such as polyethylene terephthalate, and polyamides such as nylon; non-woven fabrics, woven fabrics or laminates of these with a film of the above synthetic resin or a film of polyethylene terephthalate film having a thickness of 15 µm or less. Among these, non-woven fabrics are used particularly preferably. Non-woven fabrics can readily impart oral adhesive preparation with moderate flexibility that is desirable therefore and are useful for improving the handling property of sections of adhesive preparation, for preventing the strike-through of medicine-containing pressure-sensitive adhesive layer, and for relieving the feeling of non-self upon application of oral mucous membrane, in particular for relieving the feeling of non-self in the state where they are applied.

As the non-woven fabric, those composed of at least one fiber selected from chemical fibers such as viscose rayon, copper ammonia rayon, diacetate, triacetate, Promix (copolymer of milk casein and polyacrylonitrile), nylon, polyvinyl alcohol, polyvinylidene chloride, polyvinyl chloride, polyester, polyacrylonitrile, polyolefins, e.g., polyethylene and polypropylene, polyurethane, poly(alkylene-para-oxybenzoate), polychlal (1:1 mixture of polyvinyl chloride and polyvinyl alcohol), and natural fibers such as cotton, wool, silk, and hemp. In particular, from the viewpoints of stability, safety, and economics, non-woven fabrics composed mainly of at least one of a polyolefin fiber and a polyester fiber are preferred. Further, split fibers composed of two different components may be used. Split fiber is a fiber in which is composed of two components, for example, polypropylene and polyester, kneaded continuously along the length and which is split along the length in the process of producing non-woven fabric by extracting one of the components or by giving strong shock to it to obtain finer fibers.

The method for producing non-woven fabric is not particularly limited but includes various processes used for producing medical products, for example, a dry binder process, a thermal bond process, a spun bond process, a spun lace process, an air lay process, a needle punch process, TCF (Textile, continuously formed) process, Bemliese process, wet process, melt blown process, etc. From the viewpoints of elasticity, those produced by spun lace process are used preferably. Spun lace non-woven fabric is produced by a production process in which fibers are entangled without using binders, the process being usually expressed as spun lace, water punch, water jet, jet bond, etc.

The non-woven fabric is preferably one having a basis weight of 20 to 150 g/m$^2$, more preferably 50 to 120 g/m$^2$, as prescribed in JIS L1085. If the basis weight is smaller than the above range, the adhesive preparation generally is too flexible and the adhesive preparation tends to show decreased handling properties and there is the fear that the medicine or the medicine-containing pressure-sensitive adhesive layer will strike-through from the substrate although the degree of such strike-through may vary depending on the medicine and the kind or material of the adhesive polymer. If the basis weight is larger than the above range, the adhesive preparation will have increased cushioning properties but generally stiff as a whole and tends to give the user the feeling of the existence of foreign matter.

Even if the fiber falls within the above range of basis weight, too high a fiber density decreases the elasticity of the fiber to reduce follow-up propertiesalong unevensurfaces. On the contrary, if it is too low, the entanglement of fibers is insufficient so that falling off the fibers tends to occur. Therefore, it is preferred that non-woven fabric has a thickness of 0.1 to 1.0 mm, more preferably 0.2 to 0.8 mm, as prescribed in JIS L1085.

Further, it is preferred that non-woven fabric has a bending resistance of 10 to 80 mm, more preferably 30 to 70 mm, as prescribed in JIS L1085 (according to the 45° cantilever method). In the case of the film laminates of the above porous film or sheet, non-woven fabric and/or woven fabric with the above synthetic resins or film laminates with the polyethylene terephthalate film having a thickness of 10 μm ore less, the thickness of the laminate is preferably 0.1 to 1 mm, more preferably 0.2 to 0.8 mm.

In the present invention, the adhesive polymer which is used in the medicine-containing pressure-sensitive adhesive layer and which dissolves in an amount of 5% by weight or less in a sufficient amount of water at 20° C. and shows pressure-sensitive adhesiveness at normal temperature includes, for example, pressure-sensitive adhesives composed of acrylic polymer; rubber-based pressure-sensitive adhesives such as styrene-isoprene-styrene block copolymer, styrene-butadiene-styrene block copolymer, polyisoprene, polyisobutylene, and polybutadiene; silicone pressure-sensitive adhesives such as silicone rubber, dimethylsiloxane base, and diphenyl siloxane base; vinyl ether-based pressure-sensitive adhesives such as polyvinyl methyl ether, polyvinyl ethyl ether, and polyvinyl isobutyl ether; vinyl ester-based pressure-sensitive adhesive such as vinyl acetate-ethylene copolymer; polyester-based pressure-sensitive adhesives composed of a carboxylic acid component such as dimethyl terephthalate, dimethyl isophthalate, and dimethyl phthalate and a polyhydric alcohol component such as ethylene glycol; etc.

Preferably, at least one member selected from pressure-sensitive adhesives composed of acrylic polymers, rubber-based pressure-sensitive adhesives, silicone-based pressure-sensitive adhesives, vinyl ether-based pressure-sensitive adhesives, and vinyl ester-based pressure-sensitive adhesives are used. Among them, particularly preferred is a pressure-sensitive adhesive composed of an acrylic polymer from the viewpoints of adhesiveness to the mucous membrane in the oral cavity, solubility of medicines, stability of medicines, etc.

The above-mentioned acrylic polymer is obtained by copolymerizing (meth)acrylic acid alkyl ester used in a usual acrylic-based pressure-sensitive adhesive as a major component with one or more functional monomers. The (meth)acrylic acid alkyl ester which can be used are those in which the alkyl group specifically includes a linear alkyl group or branched alkyl group having 4 to 13 carbon atoms such as butyl, pentyl, hexyl, heptyl, octyl, 2-ethylhexyl, nonyl, decyl, undecyl, dodecyl, and tridecyl. These may be used singly or two or more of them may be used in combination. The above (meth)acrylic acid ester is not limited to the above-mentioned specific examples but (meth)acrylic acid alkyl ester having 1 to 3 carbon atoms or (meth)acrylic acid alkyl ester having 14 or more carbon atoms may be used in combination within the ranges where the properties of the present invention are not damaged. The functional monomers copolymerizable with the above (meth)acrylic acid alkyl ester are monomers having at least one unsaturated double bond that participates in copolymerization reaction in the molecule and a functional group in a side chain.

Such a functional monomer includes carboxyl group-containing monomer such as (meth)acrylic acid, itaconic acid, and maleic acid; hydroxyl group-containing monomers such as (meth)acrylic acid, hydroxyethyl ester, (meth)acrylic acid, and hydroxypropyl ester; sulfonyl group-containing monomers such as styrenesulfonic acid, allylsulfonic acid, sulfopropyl (meth)acrylate, (meth)acryloyloxy naphthalenesulfonic acid, and acrylamido methylpropanesulfonic acid; amino group-containing monomers such as (meth)acrylic acid aminoethyl ester, (meth)acrylic acid dimethylaminoethyl ester, and (meth)acrylic acid tert-butylaminoethyl ester; amido group-containing monomers such as (meth)

acrylamide, dimethyl-(meth)acrylamide, N-methylol(meth)acrylamide, N-methylolpropane(meth)acrylamide, and N-vinylacetamide; alkoxyl group-containing monomers such as (meth)acrylic acid methoxyethyl ester, (meth)acrylic acid ethoxyethyl ester, (meth)acrylic acid methoxyethylene glycol ester, (meth)acrylic acid methoxydiethylene glycol ester, (meth)acrylic acid methoxypolypropylene glycol ester, and (meth)acrylic acid tetrahydrofuryl ester; and so on. In addition to these, copolymerizable monomers include, for example, (meth)acrylonitrile, vinyl acetate, vinyl propionate, N-vinyl-2-pyrrolidone, methylvinylpyrrolidone, vinylpyridine, vinylpiperidone, vinylpyrimidine, vinylpiperazine, vinylpyrrole, vinylimidazole, vinylcaprolactam, vinyloxazole, vinylmorpholine, etc.

Among the acrylic polymers obtained by copolymerizing one or more of the above main component monomers and one or more of the functional monomers, copolymers of (meth)acrylic acid alkyl ester and (meth)acrylic acid can be used advantageously. This is because the copolymers of (meth)acrylic acid alkyl ester and (meth)acrylic acid are particularly excellent in adhesive properties such as pressure-sensitive adhesiveness and cohesiveness, and in releasability of the medicine contained in the pressure-sensitive adhesive layer. From such viewpoints, the above copolymers are more preferably copolymers obtained by copolymerizing 65 to 99% by weight of (meth)acrylic alkyl ester with 1 to 35% by weight of (meth)acrylic acid.

In the pressure-sensitive adhesive layer may if desired be blended known additives such as tackifiers (for example, rosin, modified rosin, petroleum-based resins, polyterpene resins, polystyrene resins, liquid polyisobutylene, etc) for further improving the adhesiveness, plasticizers (for example, liquid paraffin, etc.), absorption promoters, surfactants, fillers and the like.

The medicines may be contained in a dissolved state, in an oversaturated state where crystals precipitated, or in a dispersed state depending on their pharmacological effects (uses or applications). By so doing, oral adhesive preparation for the therapy and/or prophylaxis of various diseases can be obtained.

As described above, in the medicine-containing pressure-sensitive adhesive layer in the present invention, the affinity of the adhesive for the medicine is relatively low so that the medicine exhibits its effect in a relatively short time after the application and the pressure-sensitive adhesive layer has weak adhesiveness to the mucous membrane in the oral cavity so that it can be detached without difficulty. It is desirable that the administration of medicines in the therapeutic action in the region of dentistry be performed in a short time. Therefore, the oral adhesive preparation of the present invention is suitable for administration of local medicines, in particular local anesthesia whose administration time is desired to be as short as possible.

Local medicines that are administered in a short time as contained in the pressure-sensitive adhesive layer includes, for example, local anesthesia such as lidocaine, antibiotics for dentistry such as tetracycline hydrochloride, disinfectants such as cetylpyridinium chloride, oral infection preventive/therapeutic agent such as chlorohexidine hydrochloride, antiinflammatory agent such as azulene and the like.

The above local anesthesia includes besides lidocaine, cocaine, procaine, chloroprocaine, tetracaine, benzocaine, mepivacaine, prilocaine, bupivacaine, dibucaine, propoxycaine, etidocaine, dichlonine, etc. At least one substance selected from the group consisting of the above exemplary substances including lidocaine and pharmacologically acceptable salts thereof can be used in the present invention.

Further, the oral adhesive preparation basically has weak adhesiveness to the oral mucous membrane but it is possible to attach it to the mucous membrane for a time sufficient for a medicine to be absorbed through the mucous membrane when the moisture such as saliva is removed satisfactorily from the surface of the mucous membrane at its application site in the oral cavity so that the residual amount of moisture is very small amount. Therefore, use of the oral adhesive preparation of the present invention in administering systemic medicines is also expected. In the case where it is applied to outer side surface of the upper or lower gingiva, the lip holds the adhesive preparation so that a long time attachment of the adhesive preparation is possible. This makes it possible to administer systemic medicines over a long time.

The systemic medicines to be contained in the pressure-sensitive adhesive layer here includes various systemic medicines, for example, corticosteroids, analgesic antiphlogistics, narcotic sedatives, tranquilizers, antihypertensives, hypotensive diuretics, antibiotics, systemic anesthesia, antibacterial agents, antifungal agents, vitamins, coronary vessel dilators, antihistamines, expectorants, sex hormones, antidepressants, brain circulation improvers, antiemetics, antineoplastics, antiulcers, biomedicines, etc.

The thickness of the pressure-sensitive adhesive layer is usually 10 to 200 $\mu$m, preferably 15 to 150 $\mu$m. The contents of the medicine in the layer may be set appropriately depending on the kind of medicine and purpose of administration. Usually, the pressure-sensitive adhesive layer contains about 1 to 80% by weight, preferably 2 to 70% by weight, of the medicine. If the content is less than 1% by weight, the release of medicine in an amount effective for the therapy or prophylaxis is not expected. On the other hand, if the content exceeds 80% by weight, the adhesiveness decreases and the adhesive preparation will become difficult to apply so that therapeutic and prophylactic effects are limited to some extent and also economically disadvantageous.

In the present invention, the adhesive polymer constituting the pressure-sensitive adhesive layer is selected depending on the purpose of administration. More particularly, when administration in a short time is intended, the adhesive polymer that has excellent releasability of a medicine contained therein. On the contrary, when a long time administration is intended, it is desirable to select an adhesive polymer having relatively slow releasing property for the medicine contained therein.

In the present invention, in either of the adhesive preparation intended for short time administration or that intended for long time administration, the pressure-sensitive adhesive layer does not dissolve or swell so that detachment or falling off of the pressure-sensitive adhesive layer or seeping or flowing away of the medicine from the pressure-sensitive adhesive layer are difficult to occur, ensuring satisfactory availability of medicine. Further, since no deformation due to the swelling of pressure-sensitive adhesive layer occurs, the adhesive preparation of the present invention gives substantially no feeling of non-self in its applied state.

From the balance between the handling property and usability, the oral adhesive preparation of the present invention has a bending resistance (45° cantilever method) of 15 to 60 mm, preferably 20 to 50 mm, as prescribed in JIS-L1085 when measured taking the pressure-sensitive adhesive layer and substrate in combination. Here, according to the 45° cantilever method as prescribed in JIS-L1085, a test piece is placed on a horizontal stage having on one end thereof a downward slope at an angle of 45° with respect to horizontal plane and the test piece is gently slid toward the slope. When a central point of one end of the test piece has reached the slope, the distance (mm) along which the test piece has moved is measured. This value (mm) indicates bending resistance. If the bending resistance is lower than this range, the handling property tends to decrease. For example, it is difficult to apply the adhesive preparation in the oral cavity where the teeth portion and tongue portion form a narrow and complicated spatial arrangement. If the bending resistance is higher than the above range, the adhesive preparation tends to give the user a feeling of non-self upon its application.

The production method of the oral adhesive preparation of the present invention is not particularly limited. For example, mention may be made of a method which involves dissolving or dispersing a medicine, adhesive polymer, etc. in a solvent, coating the resultant solution or dispersion on at least one surface of a substrate, drying the coating to form a pressure-sensitive adhesive layer on at least one surface of the substrate.

Further, the adhesive preparation of the invention can be prepared by a method which involves coating the above solution or dispersion on a release liner, drying the solution or dispersion to form a pressure-sensitive adhesive layer on the release liner, and boding the pressure-sensitive adhesive layer on the release liner to a substrate.

Construction of the adhesive preparation in a form provided with the above release liner prevents the pressure-sensitive adhesive layer from unexpected contact with an instrument or vessel and adhesion thereto when it is produced, transported or stored. Further, since the exposed surface of the pressure-sensitive adhesive layer is coated and protected with a release liner until immediately before the application to the mucous membrane in the oral cavity and the release liner is removed for the first time when applying the pressure-sensitive adhesive layer to the mucous membrane in the oral cavity, the deterioration of the adhesiveness of pressure-sensitive adhesive layer or deterioration of the medicine can be prevented.

The material of release liner is not particularly limited so far as it can be readily detached from the pressure-sensitive adhesive layer upon use. For example, films of synthetic resin such as polyester, polyvinyl chloride, polyvinylidene chloride, polyethylene, polypropylene, and polyethylene terephthalate, papers such as high quality paper, glassine paper, and coated paper, laminated films obtained by laminating a film of plastic such as polyolefin on paper such as high quality paper or glassine paper, the films, papers or laminate films being subjected to release treatment by coating a silicone resin or a fluoro resin on the surface that contacts the pressure-sensitive adhesive layer. The thickness of the release liner is usually 10 to 200 $\mu$m, preferably 50 to 100 $\mu$m.

The shape of the oral adhesive preparation of the present invention is not particularly limited so far as it substantially allows its application. For example, mention may be made of circular, elliptic, rectangular, square, triangular, hexagonal, etc. shapes. Rectangular and square shapes are preferred from the viewpoint that physicians can handle them without difficulty. The size of the oral adhesive preparation of the present invention is one that is suitable for its application in the oral cavity. For example, when the adhesive preparation is in a shape of a rectangle, its size is 0.5 to 2 cm (in a shorter edge) by 1 to 5 cm (in a longer edge), preferably 0.8 to 1.5 cm (in a shorter edge) by 2 to 4 cm (in a longer edge). When the adhesive preparation is a square, each edge is 0.5 to 2 cm, preferably 0.8 to 1.5 cm.

As described above, when the oral adhesive preparation of the present invention is applied, it is preferred that the moisture such as saliva at and near the site of application be preliminarily removed by suction, wiping or drying by use of an air syringe (a syringe-type apparatus for drying a site of operation in the oral cavity by jetting compressed air).

When the oral adhesive preparation of the present invention contains a local medicine, it is applied to gingiva and the medicine exhibits its effect immediately. When it contains a systemic medicine, it is applied to buccal mucous membrane, mucous membrane of backside of lip, hypoglottis, gingiva, etc., from which moisture has been sufficiently removed and the effect of medicine lasts on the order of from several minutes to several hours. Further, when the oral adhesive preparation of the present invention that contains a systemic medicine is applied to the mucous membrane of backside of upper lip or outer side of the upper jaw gingiva from which moisture has been sufficiently removed, there occurs less contact with saliva and the lip and gum hold it, so that the effect of the medicine lasts for a longer time.

Generally, when the oral adhesive preparation is used in the field of actual therapy, product forms having better handling property are desired.

For example, as an oral therapy that uses local anesthetic, mention is made of surface anesthesia in the region of dentistry. The indication of dental surface anesthetic includes (a) anesthesia on the mucous membrane at the site where a needle is inserted upon infiltration anesthesia or transmission anesthesia in the main, and further (b) anesthesia of superficial, small range gingival abscess incision site, (c) anesthesia upon scaling or of inner walls of pocket upon periodontal pocket curettage, (d) anesthesia upon filling extending to gingival margin or crown prosthesis, (e) anesthesia of patients who shows vomiting reflex or gag reflex to the oral contact of dental apparatus, (f) anesthesia upon exodontics of a highly fluctuating tooth such as primary tooth at a substitution stage or upon tooth fracture and removal, (g) removal of pain of dry socket, oral mucous membrane ulcer, aphtha or other injuries, (h) removal of pain of gingiva upon attachment of rubber dam clamp, (i) anesthesia upon attachment or detachment of a metal wire splint, and the like.

The infiltration anesthesia or transmission anesthesia in (a) above is performed in order to relieve pain accompanying tooth extraction or treatment of a decayed tooth and a solution of medicine is injected at about 3 to 4 places for a single tooth to be treated. Since usually 1 or 2 teeth are treated in a single treatment, injection for infiltration anesthesia or transmission anesthesia is to be practiced sometimes at as many as about 10 sites. It is anticipated that the range of application of surface anesthesia in (b) to (i) above covers from a relatively narrow portion to the whole gingiva.

Further, when an adhesive preparation that accompanies no pain is used instead of injection in such a dental surface anesthesia, ten and several sections of adhesive preparation are required for a single treatment. Therefore, from the viewpoint of handling property in the field of therapy, it is a desirable form that one sheet mounts ten and several sections of adhesive preparation.

Further, at the time of actual operation, sections mounted on one sheet is detached and removed from the sheet with a pincette or fingers and applied to the application site in the oral cavity and hence the sheet that mounts the sections must have appropriate self-supporting property (so-called stiffness).

Referring to FIG. 1, an oral adhesive preparation 10 of the present invention includes a separator 1, and sections (adhesive sections) 2, preferably having the above-described construction, arranged on the separator 1, the sheet 10 having a prehension part 3 on a corner thereof. From the viewpoint of improved handling property, the sections 2 are arranged on the separator 1 in 2 to 5 columns, preferably 2 to 4 columns, and 2 to 5 rows, preferably 3 to 5 rows, with the columns and rows being at a substantially identical distance one from another. If the sections are arranged in a single column or row, the number of sections on one separator is too small and a separator having a long vertical or horizontal edge is required if a sufficient number of sections are to be mounted in such a single row or column arrangement. Such an arrangement is unsuitable for use. If 6 or more columns or rows are arranged, the separator will bend down too much due to the weight of the sections mounted thereon so that a problem occurs in the handling property of adhesive sections.

Further, it is preferred that the distance between any two adjacent sections be adjusted such that the proportion of the minimum inner diameter, Dp, of an incircle passing the center of gravity, W, of a section to the shortest distance, Di, of an adjacent section be 1.5 to 6, preferably 2 to 5. Usually, the adhesive preparation sheet is prepared by laminating on a separator an adhesive sheet composed of a flexible substrate having formed on one surface thereof a medicine-containing pressure-sensitive adhesive layer to form a raw fabric, punching only the adhesive sheet into a plurality of sections, and detaching and removing the adhesive sheet portions between the sections, which portions are unnecessary. That is, so-called trimming is performed. On this occasion, if the distance between any adjacent two sections is too small, trimming is not performed certainly while too large a distance between them causes the problem that the sections are detached from the separator. Merely adjusting the inter-section distance does not dissolve the problems but the balance between the size of section and inter-section distance is important. From this viewpoint, the above ratio of Dp/Di is important.

The size of the oral adhesive sheet of the present invention is limited to some extent since it is to be applied in the oral cavity and the above Dp is on the order of 2 to 20 mm, preferably 4 to 15 mm. In particular, when sections of the adhesive sheet of the present invention are applied to the mucous membrane of gingiva, it is preferred that the sections be in a size of 5–13 mm×5–13 mm.

The oral adhesive sheet of the present invention is used by detaching the sections from the separator before they can be applied to the mucous membrane of the oral cavity. On this occasion, the adhesive sheet must have a suitable flexibility in view of handling property upon detachment of the sections from the separator. In other words, in the present invention, it is desirable to adjust such that the oral adhesive sheet will show an angle of deflection of 10 degrees or less, preferably 8 degrees or less, when held horizontally at a prehension width of 5 mm at one of two points on the peripheral portion of the separator defining the largest linear length in order to retain suitable stiffness.

The oral adhesive sheet having the above-described construction is excellent in handling property upon detaching the sections from the separator and at the same time, arrangement of sections having each a suitable size mounted in a number required for in the field of actual therapy will reduce operation time for the therapy. Further, the proportion of the size of each section to the inter-section distance set to a specified value increases processability upon production to thereby increase productivity.

In the oral adhesive sheet of the present invention, the material the substrate for adhesive sections formed on the separator is not limited to water-insoluble materials but water-soluble materials such as polyvinyl alcohol, polyvinylpyrrolidone, poly-N-vinylacetamide, polyethylene oxide, polyacrylamide, polyacrylic acid salts, agar, and xanthane gum, so far as they are nontoxic.

Further, in the oral adhesive sheet of the present invention, the adhesive for sections for the oral adhesive sheet formed on the separator is not particularly limited but may be any of those which exhibit pressure-sensitive adhesiveness in a normal state, those which exhibit pressure-sensitive adhesiveness under moist conditions, those which exhibit pressure sensitive adhesiveness under heating so far as they can adhere to the oral cavity, in particular oral mucous membrane, further gingival mucous membrane for a desired time. More particularly, water-soluble adhesives composed mainly of polyvinyl alcohol, polyvinylpyrrolidone, poly-N-vinylacetamide, polyethylene oxide, polyacrylamide, polyacrylic acid salts, agar, xanthane gum, etc. water-swellable adhesives composed mainly of cross-linked water-soluble polymers, ethylcellulose, hydroxypropylcellulose, alginic acid esters, etc., can be used similarly to the non-water-soluble adhesives such as acrylic-based polymers, rubber-based polymers, silicone-based polymers, vinyl ether-based polymers, vinyl ester-based polymers, etc. In the case where of these adhesives, those which adhere to a dry surface but does not adhere to a wet surface are used, it is advantageous that the surface of mucous membrane to which the sections will be applied is air-dried before the sections can be applied thereto.

EXAMPLES

Hereinafter, the present invention will be explained in detail by examples and comparative examples. However, the present invention is not limited thereto. In the following description, "part" or "parts" are all by weight. The basis weight and thickness of non-woven fabric were values measured by the methods prescribed in JIS-L1085 and the bending resistance of the substrate and that of a combination of the substrate and pressure-sensitive adhesive layer were values measured by the method prescribed in JIS-L1085 (45° cantilever method).

[Preparation of Pressure-Sensitive Adhesive solution A]

Under an inert gas atmosphere, 95 parts of 2-ethylhexyl acrylate and 5 parts of acrylic acid were copolymerized in ethyl acetate to prepare pressure-sensitive adhesive solution A.

[Preparation of Pressure-Sensitive Adhesive Solution B]

Under an inert gas atmosphere, 50 parts of 2-ethylhexyl acrylate, 25 parts of vinylpyrrolidone, and 25 parts of vinyl acetate were polymerized in a manner similar to the operation for the pressure-sensitive adhesive solution A to prepare pressure-sensitive adhesive solution B.

[Preparation of Pressure-Sensitive Adhesive Solution C]

Under an inert gas atmosphere, 65 parts of 2-ethyihexyl acrylate, 30 parts of vinylpyrrolidone, and 5 parts of acrylic acid were polymerized in a manner similar to the operation for the pressure-sensitive adhesive solution A to prepare pressure-sensitive adhesive solution C.

[Preparation of Rubber-based Polymer D]

Fifty (50) parts of polyisobutylene (viscosity average molecular weight: 120,000), 30 parts of polyisobutylene (viscosity average molecular weight: 60,000), and 20 parts of alicyclic-based petroleum resin (softening point: 100° C.) were uniformly mixed in hexane to prepare solution D of rubber-based polymer.

Example 1

Forty (40) parts (solids content) of pressure-sensitive adhesive solution A and 60 parts of lidocaine were mixed and dissolved. The resultant solution was coated to a thickness of about 20 $\mu$m (dry basis) on a polyester separator (75 $\mu$m) and dried to form a pressure-sensitive adhesive layer. Then, the pressure-sensitive adhesive layer was laminated on a mixed-fiber non-woven fabric composed of polypropylene and polyester (thickness: 0.5 mm, basis weight: 90 g/m$^2$) to prepare an oral adhesive preparation for local anesthesia of the invention. Upon measurement of the bending resistance of non-woven fabric and that of the oral adhesive preparation (a combination of the non-woven fabric and pressure-sensitive adhesive layer), it revealed that the bending resistance of the non-woven fabric was 57 mm, and that of the oral adhesive preparation was 42 mm. Upon application of a square section (1 cm×1 cm) of the adhesive preparation to an outer side of upper jaw gingiva of a patient, it could be applied with sufficient operability (handling property), it gave the patient substantially no feeling of non-self in an applied state, it exhibited sufficient anesthetic effect 2 minutes after the application, and it could be detached without difficulty. In this case, evaluations of the usability and anesthetic effect were based on organoleptic evaluations by 5 volunteers (examinees) and evaluation of application operability (handling property) was based on organoleptic evaluation by the application operator. The anesthetic effect was confirmed by checking if 5 examinees felt pain when they were given stimulation by needle on their gingiva portions. In relation to the anesthetic effect, all the 5 examinees felt no pain by the needle.

Example 2

Forty (40) parts (solids content) of pressure-sensitive adhesive solution A and 60 parts of lidocaine were mixed and dissolved. The resultant solution was coated to a thickness of about 20 $\mu$m (dry basis) on a polyester separator (75 $\mu$m) and dried to form a pressure-sensitive adhesive layer. Then, the pressure-sensitive adhesive layer was laminated on a polypropylene non-woven fabric (thickness: 0.6 mm, basis weight: 100 g/m$^2$) to prepare an oral adhesive preparation for local anesthesia of the invention. Upon measurement of the bending resistance of non-woven fabric and that of the oral adhesive preparation (a combination of the non-woven fabric and pressure-sensitive adhesive layer), it revealed that the bending resistance of the non-woven fabric was 33 mm, and that of the oral adhesive preparation was 30 mm. Using a square section (1 cm×1 cm) of the adhesive preparation, evaluation tests were conducted in the same manner as in Example 1, and good results similar to those obtained in Example 1 were obtained.

Example 3

Forty (40) parts (solids content) of pressure-sensitive adhesive solution A and 60 parts of lidocaine were mixed and dissolved. The resultant solution was coated to a thickness of about 20 $\mu$m (dry basis) on a polyester separator (75 $\mu$m) and dried to form a pressure-sensitive adhesive layer. Then, the pressure-sensitive adhesive layer was laminated on a polyethylene film (thickness: 40 $\mu$m) to prepare an oral adhesive preparation for local anesthesia of the invention Upon measurement of the bending resistance of polyethylene film and that of the oral adhesive preparation (a combination of the polyethylene film and pressure-sensitive adhesive layer), it revealed that the bending resistances of the non-woven fabric and of the oral adhesive preparation were 21 mm and 17 mm, respectively. Upon application of a square section (1 cm×1 cm) of the adhesive preparation to an outer side of upper jaw gingiva of a patient, it could be applied with sufficient operability (handling property), it gave the patient substantially no feeling of non-self in an applied state, it exhibited sufficient anesthetic effect 2 minutes after the application, and it could be detached without difficulty. In this case, the evaluations were conducted in the same manner as in Example 1. In relation to the anesthetic effect, all the 5 examinees felt no pain by the needle.

Example 4

Ninety-five (95) parts (solids content) of pressure-sensitive adhesive solution B and 5 parts of tetracaine were mixed and dissolved. The resultant solution was coated to a thickness of about 40 $\mu$m (dry basis) on a polyester separator (75 $\mu$m) and dried to form a pressure-sensitive adhesive layer. Then, the pressure-sensitive adhesive layer was laminated on an ethylene-vinyl acetate copolymer film (thickness: 50 $\mu$m) to prepare an oral adhesive preparation for local anesthesia of the invention. Upon measurement of the bending resistances of ethylene-vinyl acetate copolymer film and of the oral adhesive preparation (a combination of the ethylene-vinyl acetate copolymer film and pressure-sensitive adhesive layer), it revealed that they had bending resistances of 18 mm and 16 mm, respectively. Upon application of a rectangular section (1 cm×3 cm) of the adhesive preparation to an outer side of upper jaw gingiva of a patient, it could be applied with sufficient operability (handling property), it gave the patient substantially no feeling of non-self in an applied state, it exhibited sufficient anesthetic effect 10 minutes after the application, and it could be detached without difficulty. In this case, the evaluations were conducted in the same manner as in Example 1. In relation to the anesthetic effect, all the 5 examinees felt no pain by the needle.

Example 5

To 70 parts (solids content) of pressure-sensitive adhesive solution C were added 20 parts of isopropyl myristate and 10 parts of lidocaine hydrochloride and then these were mixed and dissolved. The resultant solution was coated to a thickness of about 40 $\mu$m (dry basis) on a polyester separator (75 $\mu$m thick) and dried to form a pressure-sensitive adhesive layer. Then, the pressure-sensitive adhesive layer was laminated on a polyester film (about 2 $\mu$m thick)-laminated polyester non-woven fabric (thickness: 600 $\mu$m, basis weight: 100 g/m$^2$) to prepare an oral adhesive preparation for local anesthesia of the invention. Upon measurement of the bending resistances of polyester film-laminated polyester non-woven fabric and of the oral adhesive preparation (a combination of the polyester film-laminated polyester non-woven fabric and pressure-sensitive adhesive layer), it revealed that they had bending resistances of 69 mm and 44 mm, respectively. Upon application of a circular section (1 cm in diameter) of the adhesive preparation to an outer side of upper jaw gingiva of a patient, it could be applied with sufficient operability (handling property), it gave the patient substantially no feeling of non-self in an applied state, it exhibited sufficient anesthetic effect 10 minutes after the application, and it could be detached without difficulty. In this case, the evaluations were conducted in the same manner as in Example 1. In relation to the anesthetic effect, all the 5 examinees felt no pain by the needle.

Example 6

To 60 parts (solids content) of rubber-based polymer solution D were added 30 parts of isopropyl myristate and 10 parts of benzocaine and then these were mixed and dissolved. The resultant solution was coated to a thickness of about 40 μm (dry basis) on a polyester separator (75 μm thick) and dried to form a pressure-sensitive adhesive layer. Then, the pressure-sensitive adhesive layer was laminated on a polytetrafluoroethylene film (about 60 μm thick) to prepare an oral adhesive preparation for local anesthesia of the invention. Upon measurement of the bending resistances of polytetrafluoroethylene film and of the oral adhesive preparation (a combination of the polytetrafluoroethylene film and pressure-sensitive adhesive layer), it revealed that they had bending resistances of 37 mm and 30 mm, respectively. Upon application of a rectangular section (1 cm×3 cm) of the adhesive preparation to an outer side of upper jaw gingiva of a patient, it could be applied with sufficient operability (handling property), it gave the patient substantially no feeling of non-self in an applied state, it exhibited sufficient anesthetic effect 10 minutes after the application, and it could be detached without difficulty. In this case, the evaluations were conducted in the same manner as in Example 1. In relation to the anesthetic effect, all the 5 examinees felt no pain by the needle.

Comparative Example 1

Ninety (90) parts (solids content) of hydroxypropylcellulose solution and 10 parts of lidocaine were mixed and dissolved. The resultant solution was coated to a thickness of about 40 μm (dry basis) on a polyurethane film (100 μm thick) and dried to form an oral dental film preparation for local anesthesia. Then, the preparation was shaped to a rectangular form of a size of 1 cm×3 cm, which was applied to the outer side of upper jaw gingiva of a patient. 10 minutes after the application, it was detached. It showed swelling at its periphery and gave the examinee the feeling of non-self. Since it bonded with strong adhesion, the patient felt pain in an applied state and also felt strong pain upon its detachment. Also, the examinee felt bitter taste due to the seeping of the medicine. The anesthetic effect 10 minutes after the application was insufficient. Evaluation tests were conducted in the same manner as in Example 1. In relation to the anesthetic effect, 4 out of the 5 examinees felt pain by the needle and the remaining one felt slight pain.

Example 7

Examples 1 to 6 above are examples of oral adhesive preparations for use in administration of local anesthesia. In contrast, the present example relates to an oral adhesive preparation for use in administration an antiphlogistic. Ninety-five (95) parts (solids content) of pressure-sensitive adhesive solution B and 5 parts of azulene were mixed and dissolved. The resultant solution was coated to a thickness of about 40 μm (dry basis) on a polyester separator (75 μm thick) and dried to form a pressure-sensitive adhesive layer. Then, the pressure-sensitive adhesive layer was laminated on a polyester non-woven fabric (thickness: 0.6 mm, basis weight: 100 g/m$^2$) to prepare an oral adhesive preparation for an antiphlogistic use. Upon measurement of the bending resistances of polyester non-woven fabric and of the oral adhesive preparation (a combination of the polyester non-woven fabric and pressure-sensitive adhesive layer), it revealed that they had bending resistances of 43 mm and 29 mm, respectively. Upon application of a rectangular section (1 cm×3 cm) of the adhesive preparation to an outer side of upper jaw gingiva of a patient, it could be applied with sufficient operability (handling property), it gave the examinee substantially no feeling of non-self in an applied state, it exhibited sufficient anesthetic effect 10 minutes after the application, and it could be detached without difficulty. In this case, the evaluations were conducted in the same manner as in Example 1. (82) Examples 8 and 9 below are examples of oral adhesive preparations for the administration of systemic medicines.

Example 8

Ninety-five (95) parts (solids content) of pressure-sensitive adhesive solution C and 5 parts of diazepam were mixed and dissolved. The resultant solution was coated to a thickness of about 40 μm (dry basis) on a polyester separator (75 μm thick) and dried to form a pressure-sensitive adhesive layer. Then, the pressure-sensitive adhesive layer was laminated on a polypropylene non-woven fabric (thickness: 0.6 mm, basis weight: 100 g/m$^2$) to prepare an oral adhesive preparation for use in administering an antidepressant. Upon measurement of the bending resistances of the polyester non-woven fabric and that of the oral adhesive preparation (a combination of the polyester non-woven fabric and pressure-sensitive adhesive layer), it revealed that their bending resistances were 43 mm and 29 mm, respectively. Upon application of a rectangular section (1 cm×3 cm) of the adhesive preparation to the mucous membrane of left bucca of examinees, it could be applied with sufficient operability (handling property), it gave the examinees substantially no feeling of non-self in an applied state, and it adhered to the application site even 2 hours after the application. In this case the surface of mucous membrane of left bucca was subjected to removal of moisture by use of an air syringe before the application. In this case, evaluations were based on organoleptic evaluations by 5 volunteers (examinees) and evaluation of application operability (handling property) was based on organoleptic evaluation by the application operator in the same manner as in Example 1.

Example 9

To 70 parts (solids content) of rubber-based polymer solution D were added 20 parts of isopropyl myristate and 10 parts of cimetidine were mixed and dissolved. The resultant solution was coated to a thickness of about 40 μm (dry basis) on a polyester separator (75 μm thick) and dried to form a pressure-sensitive adhesive layer. Then, the pressure-sensitive adhesive layer was laminated on a mixed-fiber non-woven fabric composed of polypropylene and polyester (thickness: 0.5 mm, basis weight: 90g/m$^2$) to prepare an oral adhesive preparation for antiulcer agent of the invention. Upon measurement of the bending resistance of polypropylene and polyester mixed-fiber non-woven fabric and that of the oral adhesive preparation (a combination of the polypropylene and polyester mixed-fiber non-woven fabric and pressure-sensitive adhesive layer), it revealed that their bending resistances were 54 mm and 41 mm, respectively. Upon application of a rectangular section (1 cm×3 cm) of the adhesive preparation to an outer side of upper jaw gingiva of a patient, it could be applied with sufficient operability (handling property), it gave the patient substantially no feeling of non-self in an applied state, it adhered to the application site even after 8 hours after the application. In this case the outer surface of mucous membrane was subjected to removal of moisture by use of an air syringe before the application. In this case, evaluations were based on organoleptic evaluations by 5 volunteers (examinees) and evaluation of application operability (handling property) was based on organoleptic evaluation by the application operator conducted in the same manner as in Example 1.

Comparative Example 2

Ninety-five (95) parts (solids content) of hydroxypropylcellulose solution and 5 parts of diazepam were mixed and dissolved. The resultant solution was coated to a thickness of about 100 μm (dry basis) on a polyurethane film (100 μm thick) and dried to form a water-swellable oral film preparation for use as an antidepressant. Upon application of a rectangular section (1 cm×3 cm) of the adhesive preparation to the outer side of the upper jaw of examinees, an edge of the preparation began to swell in 30 minutes, it swelled in 2 hours to about 15 times the original thickness, thus giving the examinee a strong feeling of non-self. The preparation fell off about 3 hours after the application. In this case the surface of mucous membrane of upper jaw gingiva was subjected to removal of moisture by use of an air syringe before the application. In this case, evaluations were based on organoleptic evaluations by 5 volunteers (examinees) and evaluation of application operability (handling property) was based on organoleptic evaluation by the application operator in the same manner as in Example 1.

Example 10

Forty (40) parts (solids content) of ethyl acetate solution of acrylic-based adhesive (copolymer of 2-ethylhexyl acrylate/acrylic acid=95/5 by weight) and 60 parts by weight of lidocaine were mixed and dissolved. The resultant solution was coated to a thickness of about 20 μm on dry basis on the treated surface of polyester separator (75 μm thick) treated with silicone on one surface thereof and dried to prepare a medicine-containing pressure-sensitive adhesive layer.

Next, the formed medicine-containing pressure-sensitive adhesive layer was laminated on one surface of the polypropylene non-woven fabric (basis weight: 100 g/m$^2$, thickness: about 0.6 mm) and this was wound to obtain a raw fabric of adhesive sheet.

Then, the raw fabric was punched only the adhesive sheet such that sections are arranged in 3 column by 4 rows as shown in FIG. 1 to obtain an oral adhesive sheet of the present invention. Each of the obtained sections has the following size.

Size of section: 10 mm square;
Distance between adjacent sections: 3 mm;
Dp/Di: 3.3:
Distance from the periphery of separator to the section: 7 mm; and
Size of separator: 63 mm×50 mm.

A corner of the separator of the resultant oral adhesive sheet (the prehension part 3 in FIG. 1) was grabbed and the degree of deflection was measured. As a result, the angle of deflection was 4.4 degrees and the operability and working efficiency when detaching each section for use were good. In the trimming step in which the adhesive sheet around the section in the production of the above-mentioned oral adhesive sheet, there occurred no cutting of unnecessary parts (dregs) around the sections nor falling-off of sections so that punching and trimming operations could be performed beneficially.

Comparative Example 3

The raw fabric of adhesive sheet obtained in Example 10 was punched into sections arranged in 3 columns by 4 rows to obtain an oral adhesive sheet of the present invention. The size of section was as follows.

Size of section: 10 mm square;
Distance between adjacent sections: 1 mm;
Dp/Di: 10:
Distance from the periphery of separator to the section: 7 mm; and
Size of separator: 46 mm×57 mm.

A corner of the separator of the resultant oral adhesive sheet (the prehension part 3 in FIG. 1) was grabbed and the degree of deflection was measured. As a result, the angle of deflection was 3.8 degrees and the operability and working efficiency when detaching each section for use were good. However, in the trimming step in which the adhesive sheet around the section in the production of the above-mentioned oral adhesive sheet, cutting of unnecessary parts (dregs) around the sections occurred and there was difficulty in the trimming operation.

Comparative Example 4

The raw fabric of adhesive sheet obtained in Example 10 was punched into sections arranged in 3 columns by 4 rows to obtain an oral adhesive sheet of the present invention. The size of section was as follows.

Size of section: 10 mm square;
Distance between adjacent sections: 8 mm;
Dp/Di: 1.25:
Distance from the periphery of separator to the section: 7 mm; and
Size of separator: 60 mm×78 mm.

A corner of the separator of the resultant oral adhesive sheet was grabbed and the degree of deflection was measured. As a result, the angle of deflection was 8.9 degrees and the operability and working efficiency when detaching each section for use were good. However, in the trimming step in which the adhesive sheet around the section in the production of the above-mentioned oral adhesive sheet was removed, the sections fell off from the separator during the trimming, resulting in product failure although no cutting of unnecessary parts (dregs) around the sections occurred.

Comparative Example 5

The raw fabric of adhesive sheet obtained in Example 1 was punched into sections arranged in 2 columns by 6 rows to obtain an oral adhesive sheet of the present invention. The size of section was as follows.

Size of section: 9 mm square;
Distance between adjacent sections: 3 mm;
Dp/Di: 3:
Distance from the periphery of separator to the section: 7 mm; and
Size of separator: 83 mm×35 mm.

A corner of the separator of the resultant oral adhesive sheet was grabbed and the degree of deflection was measured. As a result, the angle of deflection was 11.4 degrees and the sheet was deflected too much to give acceptable operability of detachment when the sections were detached for use. However, in the trimming step in which the adhesive sheet around the section in the production of the above-mentioned oral adhesive sheet was removed, neither cutting of unnecessary parts (dregs) around the sections nor falling-off of the sections occurred. As a result, punching and trimming operations could be performed beneficially.

The invention may be embodied in other specific forms without departing from the spirit or essential characteristics thereof. Therefore, the present embodiment is to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An oral adhesive sheet comprising a separator release-treated on one or both surfaces thereof and a plurality of sections for application to oral mucous membrane mounted on at least one surface of said separator, wherein said sections comprise each a flexible substrate and a pressure-sensitive adhesive layer on one surface of said substrate, wherein said sections are adhered and arranged on said separator in 2 to 5 columns by 2 to 5 arrows, each section being in a substantially equivalent distance from adjacent section, and wherein inter-section distance between any adjacent two sections is set such that a proportion of a minimum inner diameter, Dp, of an incircle passing a center of gravity, W, of a section to a shortest distance, Di, of an adjacent section is 1.5 to 6.

2. The oral adhesive sheet as claimed in claim 1, wherein said substrate is cloth.

3. The oral adhesive sheet as claimed in claim 1, wherein said sheet shows an angle of deflection of 10 degrees or less when held horizontally at a prehension width of 5 mm at one of two points on a peripheral portion of said separator defining a largest linear length.

4. The oral adhesive sheet as claimed in claim 1, wherein said section is a section for application to gingival mucous membrane.

5. The oral adhesive sheet as claimed in claim 1, wherein said pressure-sensitive adhesive layer contains a medicine, and is substantially insoluble in water or absorbs substantially no water.

6. The oral adhesive sheet as claimed in claim 1, wherein said substrate comprises a non-woven fabric that has a basis weight of 20 to 150 g/m$^2$ as prescribed in JIS-L1085 and a thickness of 0.1 to 1.0 mm as prescribed in JIS-L 1085.

7. The oral adhesive sheet as claimed in claim 6, wherein the non-woven fabric has a bending resistance (45° cantilever method) of 10 to 80 mm as prescribed in JIS-L1085.

8. The oral adhesive sheet as claimed in claim 6, wherein the non-woven fabric comprises as a major component at least one of polyolefin fiber and polyester fiber.

9. The oral adhesive sheet as claimed in claim 6, wherein the non-woven fabric is spun lace non-woven fabric.

10. The oral adhesive sheet as claimed in claim 1, wherein a combination of the pressure-sensitive adhesive layer and the substrate has a bending resistance (45° cantilever method) of 15 to 60 mm as prescribed in JIS-L1085.

11. The oral adhesive sheet as claimed in claim 1, wherein said pressure-sensitive adhesive layer that is substantially insoluble in water or absorbs substantially no water comprises at least one member selected from the group consisting of acrylic-based polymers, rubber-based adhesives, silicone-based adhesives, vinyl ether-based adhesives, and vinyl ester-based adhesives.

12. The oral adhesive sheet as claimed in claim 11, wherein the adhesive comprising an acrylic-based polymer is a copolymer of (meth) acrylic acid alkyl ester and (meth) acrylic acid.

13. The oral adhesive sheet as claimed in claim 12, wherein the copolymer of (meth) acrylic acid alkyl ester and (meth) acrylic acid comprises a copolymer of 65 to 99% by weight of (meth) acrylic alkyl ester and 1 to 35% by weight of (meth) acrylic acid.

14. The oral adhesive sheet as claimed in claim 5, wherein the medicine is a local anesthetic.

15. The oral adhesive sheet as claimed in claim 14, wherein the local anesthetic is at least one member selected from the group consisting of lidocaine, cocaine, procaine, chloroprocaine, tetracaine, benzocaine, mepivacaine, prilocaine, bupivacaine, dibucaine, propoxycaine, etidocaine, dichlonine, and pharmacologically acceptable salts thereof.

16. The oral adhesive sheet as claimed in claim 5, wherein the medicine is a systemic medicine.

17. The oral adhesive sheet as claimed in claim 16, wherein the systemic medicine is at least one member selected from the group consisting of corticosteroids, analgesic antiphlogistics, narcotic sedatives, tranquilizers, antihypertensives, hypotensive diuretics, antibiotics, system anesthesia, antibacterial agents, antifungal agents, vitamins, coronary vessel dilators, antihistamines, expectorants, sex hormones, antidepressants, brain circulation improvers, antiemetics, antineoplastics, antiulcers, and biomedicines.

* * * * *